United States Patent

Wingo et al.

[11] Patent Number: 5,545,226
[45] Date of Patent: Aug. 13, 1996

[54] IMPLANTS FOR CRANIOPLASTY

[75] Inventors: James P. Wingo, Stone Mountain; John R. Miller, Woodstock, both of Ga.

[73] Assignee: Porex Technologies Corp., Fairburn, Ga.

[21] Appl. No.: 225,345

[22] Filed: Apr. 8, 1994

Related U.S. Application Data

[63] Continuation of Ser. No. 889,905, May 29, 1992, abandoned.

[51] Int. Cl.⁶ ................................................ A61F 2/28
[52] U.S. Cl. .................................... 623/16; 623/11
[58] Field of Search ..................... 623/11, 12, 16–18, 623/20, 23; 606/60, 61, 69–74; 16/4

[56] References Cited

U.S. PATENT DOCUMENTS

| | | | |
|---|---|---|---|
| 3,158,893 | 12/1964 | Smith | 16/4 |
| 4,055,862 | 11/1977 | Farling | 623/20 |
| 4,186,448 | 2/1980 | Brekke | 623/16 |
| 4,651,724 | 3/1987 | Berentey et al. | 606/69 |
| 4,714,469 | 12/1987 | Kenna | 606/61 X |
| 4,778,469 | 10/1988 | Lin et al. | 623/20 |
| 4,863,474 | 9/1989 | Brown et al. | 623/23 |
| 4,969,904 | 11/1990 | Koch et al. | 623/16 |
| 4,979,957 | 12/1990 | Hodorek | 623/16 X |
| 4,997,432 | 3/1991 | Keller | 606/61 |
| 5,002,576 | 3/1991 | Fuhrmann et al. | 606/61 X |
| 5,002,583 | 3/1991 | Pitaru et al. | 623/16 X |
| 5,071,437 | 12/1991 | Steffee | 623/17 |
| 5,074,880 | 12/1991 | Mansat | 623/16 X |
| 5,084,051 | 1/1992 | Törmäläet al. | 623/16 X |
| 5,108,435 | 4/1992 | Gustavson et al. | 623/16 |
| 5,123,926 | 6/1992 | Pisharodi | 623/17 |
| 5,139,497 | 8/1992 | Tilghman et al. | 623/16 |
| 5,171,281 | 12/1992 | Parsons et al. | 623/17 |
| 5,348,788 | 9/1994 | White | 623/16 |

OTHER PUBLICATIONS

Craniofacial Applications for the Medpor Porous Polyethlene Flexblock Implant; Tadeusz et al., *The Journal of Craniofacial Surgery*, vol. 3, No. 2, 1992, Little Brown and Company, Boston, Massachusetts, 1992.

*Primary Examiner*—Robert A. H. Clarke
*Attorney, Agent, or Firm*—Lane, Aitken & McCann

[57] ABSTRACT

A implant for cranioplasty made of porous high density polyethylene is provided. The implant has a smooth upper surface and a lower surface characterized by a plurality of conical extensions. The implant is flexible so that it can conform to the contour of the cranium and can be cut with a scalpel or surgical scissors or bone cutters. The shape of the implant allows a surgeon to easily adapt the implant to fit into cranial defects such as those caused by harvesting bone grafts.

16 Claims, 3 Drawing Sheets

FIG. 1
FIG. 2
FIG. 3
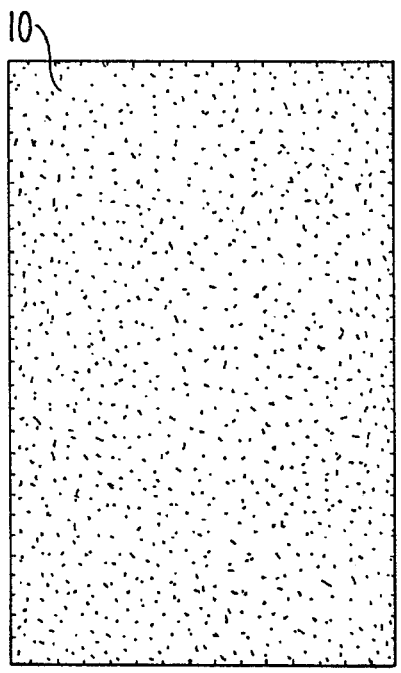
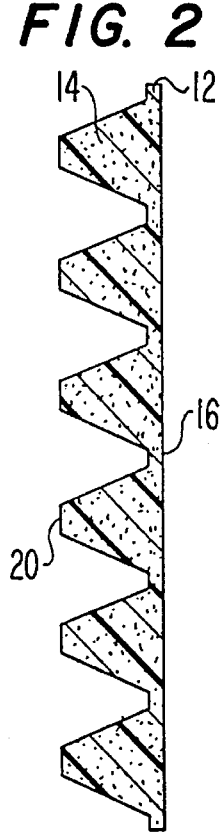
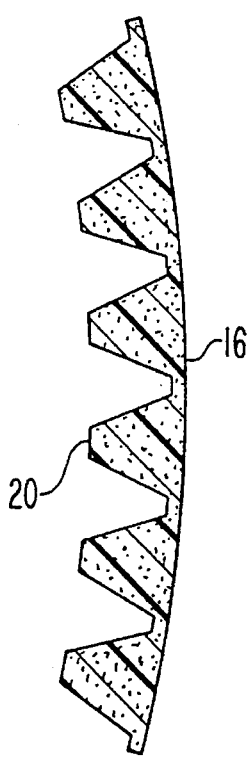
FIG. 4
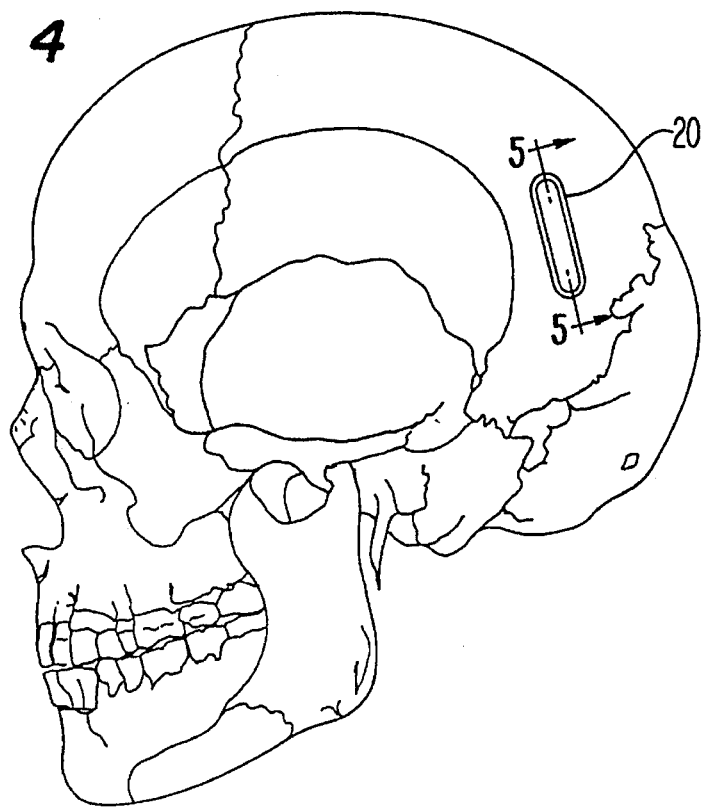

IMPLANTS FOR CRANIOPLASTY

This application is a continuation of application Ser. No. 07/889,905, filed May 29, 1992, now abandoned.

This invention relates to artificial bone implants and more specifically to implants used for cranioplasty.

BACKGROUND OF THE INVENTION

Plastic surgeons often are required to augment or repair bone structure in reconstructive surgery to correct injury or birth defects. Bone augmentations are also routinely performed in cosmetic surgery. For facial bone augmentations, surgeons will most often choose natural bone from the patient to provide graft material. These grafts, called autogenous grafts, because they are taken from the patient, allow for the ingrowth of new bone and improve the chances of graft acceptance. Autogenous grafts have several drawbacks which include the need for a second operative site. The donor site can cause considerable postoperative discomfort and unsightly depressions. These imperfections are most notably seen in graft sites in the cranium.

When a surgeon elects to harvest natural bone from the section of the cranium for a graft, after suitably preparing the epidermal layer, the surgeon first makes an incision through the scalp and connective tissue or periosteum to reveal the surface of the outer table of the cranium of the patient. Using a bone cutting tool, the surgeon cuts into the cranium but is careful not to penetrate the entire thickness of the cranium. The skull in this area is relatively thick and it is possible to obtain a bone section up to 5 mm thick from the region. The surgeon frees and removes the tissue from the area which will be later transplanted or grafted to the facial area in need of augmentation. This procedure results in the creation of defects which have varying sizes and shapes as dictated by the need for material in the operative site. The defects are irregularly shaped due to the contours of the outer surface of the cranium and the varying depth of the incisions formed by the surgeon. The defects are defined by the peripheral edges of the cranium's outer surface sidewalls which extend radially into the cranium and communicate with a bottom surface or bed. Removal of the bone compromises the protection provided by the cranium because the remaining portion of the cranium which lays beneath the bed of the tissue harvest site is thinner. Removal of the bone graft tissue also results in a ridge defined by the peripheral edges of the depression on the outer surface of the cranium. This ridge presents an undesirable risk of further injury and is cosmetically unappealing.

Cranioplasty is also necessary to correct defects in the cranium which are formed as a result of trauma and other surgery in response to disease. For example, a surgeon may cut entirely through the outer table of the cranium revealing the underlying brain in order to remove a meningioma or osteoma. The bone tissue removed by the surgeon must be replaced with a suitable replacement matrix. In cases of severe trauma, portions of the cranium may be fractured beyond use or entirely lost. Material placed in a defect of this type must be supported to ensure that it will not put pressure on the brain. In such situations, a suitable implant must be easily conformed to these sites.

Preferably, a defect caused by trauma or surgery should be completely filled with an implant which is the same size and shape of the bone tissue that has been removed or lost. In order to protect the brain, the material should be sufficiently hard, yet the implant must have some flexibility to enable it to conform to the contours of each patient's cranium. A porous material is preferred to allow for tissue ingrowth which will permanently stabilize the implant in position. Another important consideration is to provide a material which is relatively easy to shape to fit the dimensions of the void or defect so as to allow the surgeon to quickly treat the area and avoid complications.

Although natural bone is the preferred choice for many applications, it is not a practical material to treat the defects in the cranium as described above. Natural bone is difficult or impossible to shape to the desired configuration and there is not a readily available source of the material. Resorption is also a problem known to occur with natural bone or bone derived implants as well as deformation. In instances of both resorption and deformation, an implant does not retain its intended shape and further corrective surgery may be required.

In response to the need for suitable bone implant materials there have been a number of synthetic materials developed for use as artificial bone or similar support tissue. These materials have included metals, ceramics, plastics and other polymers and a number of combinations thereof. Synthetic materials are easy to obtain, maintain, can be biologically inert and do not involve additional trauma to the body. Some synthetic materials are easy to shape to desired configurations and most can be made porous like natural bone. Porous implant materials are favored because of their ability to unite with live bone fragments and allow for tissue ingrowth. Tissue ingrowth stabilizes the implant and provides strength to the interface between the implant and adjoining tissue. If foreign implant materials are left permanently in place and are not adequately stabilized they can become dislodged which can cause irritation or impairment. Biodegradable implant materials are sometimes advantageous because the they will eventually degrade and allow tissue to completely fill the void.

Alloplastic materials continue in popularity as bone implants despite relatively high complication rates and difficulty in shaping the currently available implant materials. One widely used material methylmethacrylate, a thermoplastic material, has been linked to tissue damage and the release of a toxic monomer which has been implicated in adverse reactions. Furthermore methylmethacrylate is brittle and has been connected with bone reabsorption, loosening of the implant and infection.

High density porous polyethylene has been successfully used in the reconstruction of maxillofacial trauma patents and has been specifically used for orbital reconstruction and onlay grafting. It is porous, biologically inert, relatively hard and will not degrade. Porous polyethylene is the synthetic material of choice for applications which require rigidity due to its tolerance, resistance to infection and hardness, however it can not be easily shaped to fill cranial defects. Polyethylene blocks have a low modulus of elasticity and would be difficult to shape for use in sections thick enough to treat cranial defects.

Softer plastic materials such as polytetraflouro-ethylene ("PTFE") are not suitable for use in cranioplasty because they do not provide sufficient protection until ossification is complete and ossification in compact bone tissue occurs at a very slow rate. In instances where the entire outer table is removed, ossification will only occur from the sides of the implant.

For example, Proplast™, a carveable and flexible composite material made of PTFE and carbon or aluminum oxide, has been commercially available for use as an implant however it does not provide the necessary structural integrity for cranioplastic procedures. Proplast employs a biodegradable agent which gives the material its rigid characteristics. After implantation in the body, the agent degrades and the rigid character of the material is lost. Proplast can also present complications due to the presence of carbon and aluminum oxide which are reactive. Lastly, carbon impregnated material can sometimes be seen through the skin when planted subcutaneously.

Silicone, which is popular for facial reconstructions because of its elasticity, has been custom fabricated for use in cranial contour restoration. However, silicone is not hard enough to mimic the cranium and there has been recent controversy concerning the safety of silicone as an implant material. In animals, silicone has been associated with prolonged local fluid accumulation and resorption of the underlying bone requiring the patient to undergo additional corrective surgery.

Hydroxyapatite has been a popular implant material because of it ability to provide for good bone ingrowth however its use is not a practical solution to the correction of cranial deformities. Hydroxyapatite has a low modulus of elasticity and is difficult for the surgeon to manipulate. Complications associated with this type of surgical implantation require time which is expensive and increases the chances of complications.

Polymers such as polyacetic acid as described in U.S. Pat. No. 4,186,448 have been used to successfully treat voids formed as a result of the removal of teeth or central bone tumors and treating maxillofacial trauma. Polylactic acid has been formed in thin sheets and used in place of "Teflon"™ or Superamid to provide support for the orbital floor. Polyacetic acid however degrades over time and does not provide a permanent scaffold structure to provide elevation and hardness over time.

Successful metals used as bone implants include stainless steel and titanium alloys. Initial problems associated with the lack of porosity have been overcome by employing mesh or by advanced sintering processes which leave a porous substrate. Cranioplasty with metals, such as titanium mesh, are strong and relatively inert and have been used with success in some applications. However metals are expensive, heavy, have a high thermal conductivity and are difficult to unite with live bone. They are also difficult to conform to the desired shape and have different elastic properties than that of bone.

In the past, plates made of stainless steel or various alloys have been used to cover and protect the areas of the cranium where the bone has been partially or entirely removed as a result of surgery or injury. Although metal implants are of sufficient strength and hardness to provide adequate protection, metal is difficult to shape and conform to the natural contours of the cranium and the defect. Moreover, plates are difficult to permanently affix to the cranium and leave a hollow cavity between the outer surface of the cranium and inner bed surface. Furthermore, metal plates are difficult to affix to the cranium by adhesives or other mechanical means which results in an operation requiring more time and expense.

Ceramic implants have high compression strength, chemical, biological inertness and a porous structure but have low resistance to impact loads. Ceramic materials are generally unsatisfactory for cranioplasty because they are brittle and are liable to break upon high impact or tension. Moreover ceramics are not flexible and are difficult to shape.

There is a need for a suitable device and material to fill the void left by a bone graft from the cranium or from the removal of a cranium section. Cranial contour correction and the repair of defects in the cranium has no clearly defined solution. Existing operative methods are time consuming and often yield unsatisfactory long term results. Furthermore the implant must be relatively easy to employ and present few complications. The implant must be strong, durable and bio-compatible yet should be easy to mold and shape to the dimensions of the depression or defect. The implant material should be flexible enough to roughly conform to the shape of the cranium. Preferably the material should be porous to enable the implant to receive new ingrowth of bone growth and to be secured in place.

The object of the present invention is to provide an implant design to easily fill the void in the cranium which results from autogenous graft operations. Another object of the invention is to provide a suitable implant that can be used to correct any defect in the cranium caused by trauma or other means. A further object of the invention is to provide an implant which is hard and durable, yet be flexible enough to be able to conform to the natural contours of the cranium.

A further object is to provide a device that is easy to shape to the dimensions of the void yet have sufficient hardness to serve as a protective shield. A further object of the invention is to provide a device that is porous to enable new ingrowth into the device to allow for permanent fixation.

Still another object of the invention is to provide a design which allows for both flexibility and projection.

SUMMARY OF THE INVENTION

In accordance with the invention, a thin implant with a smooth upper surface and a plurality of conical extensions projecting from the lower surface is provided. The structure allows the implant to be flexed in any direction within the range of the outer diameter of the distal end of each projection. Further flexation is prevented by the interference with neighboring cones. To properly fit in the defect in the bone, the device can be shaped so that the uneven surface on the graft bed is substantially filled with the implant material. A one-piece porous substrate of polyethylene or other plastic which can be easily cut and shaped with standard surgical scissors or a bone cutter is preferred, although the implant could be constructed of other materials.

The implant material has pores of a sufficient size and shape to allow for growth of new bone tissue into the prothesis. Bone growth can permanently affix the prothesis in the defect thereby dispensing with the need for permanent adhesives or mechanical attachment means such as screws.

BRIEF DESCRIPTION OF THE DRAWINGS

FIG. 1 is a top plan view of the implant according to the invention;

FIG. 2 is an enlarged cross section view of the implant material of the invention through the conical extensions;

FIG. 3 is a the side view of FIG. 2 in a flexed position;

FIG. 4 is a side view of a human skull showing a defect located in the side of the cranium;

DETAILED DESCRIPTION OF THE INVENTION

Figure 5:
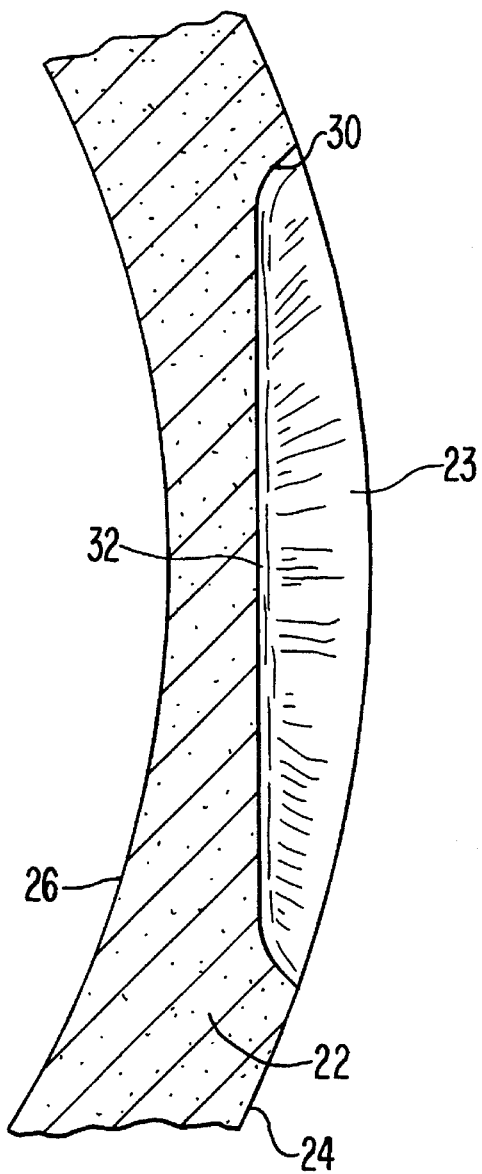
FIG. 5 is an enlarged cross section of the defect shown in FIG. 4 along axis 5—5.

As shown in FIG. 1, an implant generally designated by the reference numeral 10 is made of a porous high density plastic substrate in a rectangular configuration. The plastic material is molded to dimensions to a degree 45 mm long and 30 mm wide. In this embodiment a highly porous high density polyethylene which is commercially available under the name "MEDPOR" Surgical Implant, from Porex Technologies Corp. of Fairburn, Ga. is employed to make the implant. This material is very strong, hard, completely inert and durable over time. The material has a contiguous large pore structure which allows blood to flow through and can be rapidly vascularized to permit tissue ingrowth. MEDPOR has been available for human use since 1985 and is formed by sintering pure medical grade, high density polyethylene into virtually any preformed shape. It is strong enough to provide protection for the posterior area of the cranium. Implants of this material have shown to be highly resistant to infection and are biocompatable. Although the MEDPOR surgical implant material has worked successfully for this device a number of other high density porous plastics would also be suitable for the device.

Figure 6:
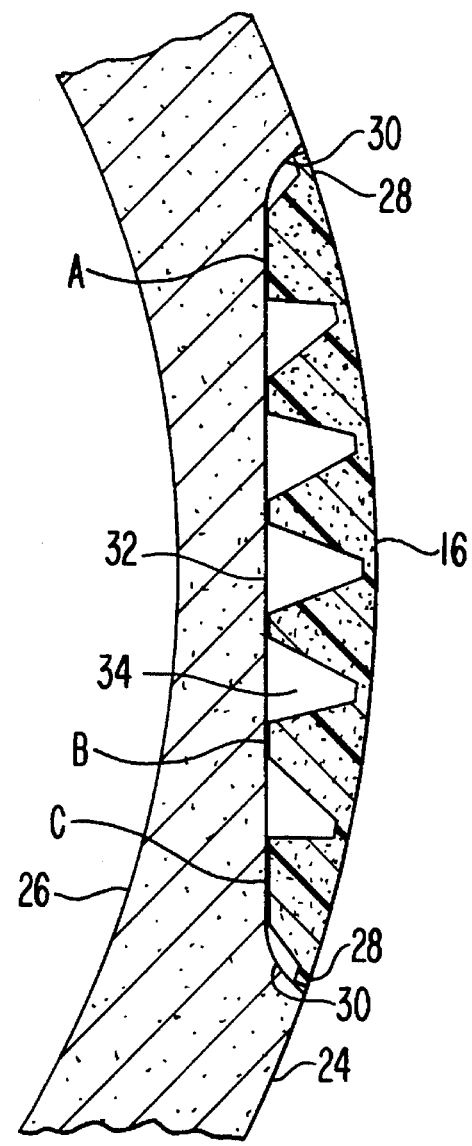
FIG. 6 is an enlarged cross section of the void shown in FIG. 5 with an implant adapted to conform to the dimensions of the defect.
Figure 7:
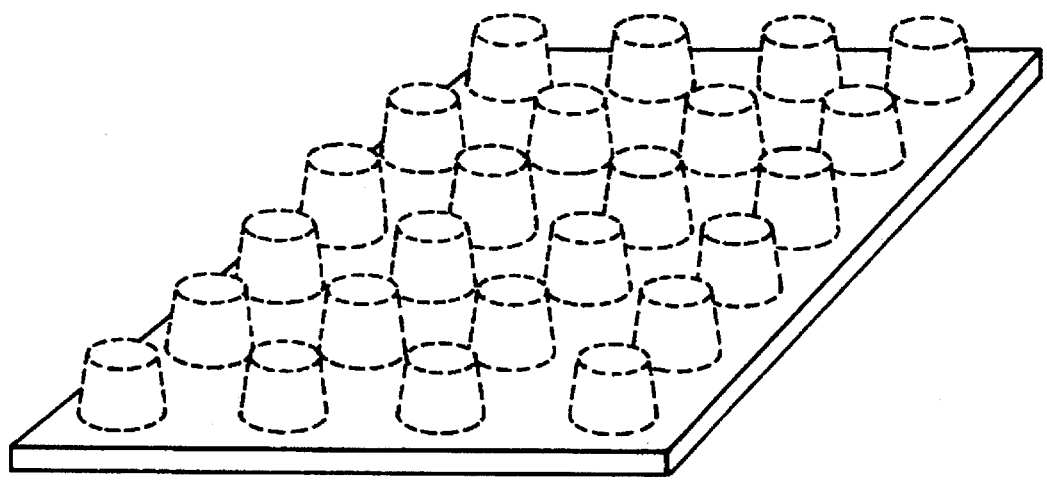
FIG. 7 is an isometric drawing of the invention showing in phantom an array of cones distributed across the lower surface of an implant in two dimensions.

A side view of the implant as shown in FIG. 2, reveals that extending from a thin the planar region 12 are a plurality of conical extensions 14. The axial dimensions of the planar region 12 is 1 mm thick which allows the material to bend and flex. When in place, the smooth upper surface 16 will be contiguous with the outer surface 18 of the outer table of the cranium as best shown in FIG. 6. The conical extensions 14 have an axial length of 3.0 mm which result in a total axial dimension or thickness of the implant of 4.0 mm. The base of each cone which communicates with the planar region 12 has a radius of 4.0 mm and the cones taper over their 3.0 mm length to an flat end 20 having a radius of 3.0 mm. In this embodiment the base of the cones are spaced approximately 1.0 mm apart. The cones and the planar surface are made of the same material and are of one piece construction. The shape of the implant provides elevation and allows for the flexibility of the implant.

Although the preferred material is comprised of a synthetic flexible porous substrate made of high density polyethylene, any flexible substrate with sufficient hardness formed with extensions would be suitable for the implant. The presence of the extensions give the implant its ability to provide for projection or thickness while maintaining a degree of flexibility which would not be obtainable from a solid substrate of material having the equal thickness. A solid material constructed of high density polyethylene having an axial dimension of 4.0 mm to 5.0 mm would not bend to the required degree to conform to the contour of the cranium. FIG. 3 shows a cross section of the implant in a flexed position. The material is able to flex at the spaces between the cones. The shape of the implant permits flexibility of the planar surface in any direction perpendicular to the planar surface. The conical extensions allow a relatively hard substrate to achieve a high profile and substantially fill a cranial defect area. The design also permits a surgeon to cut the implant with relative ease because both the planar region and conical ends are relatively thin. Thus, the surgeon can easily cut the top surface of the implant to fit the area and adjust the height by cutting the conical projections.

Although the implant was specifically intended for use on calvarial bone graft donor site deformities, the implant can be used for a variety of cranio-facial applications. FIG. 4 shows the location of a typical graft harvest site bed 20 which would remain from tissue harvesting although the graft harvest site could conceivably be from anywhere on the cranium. Cranial deformities of sizes from small to medium are best treated with this preformed implant. Larger defects could be treated by the custom construction of a similar implant based on the precise dimensions of the defect.

In operation, after a surgeon removes graft bone tissue a defect in the cranium remains. As shown in FIG. 5, an enlarged cross section of a harvest graft site 23 in the cranium 22, the defect is typically asymmetrical and has varying depths. The thickness of the cranium 22 from the outer surface 24 to the inner surface 26 is approximately 6.0 mm in the rear area of the cranium where grafts are typically harvested.

The surgeon will next cut a planar section of the implant material to roughly conform to the shape of a depression or void in the cranium. The surgeon may use a stencil to trace the shape of the defect and transfer the pattern to the upper flat surface of the implant. Using a scalpel or surgical scissors, the surgeon next trims the implant to closely conform to the shape of the defect. In the event part of the implant does not properly fit, any protruding edges can be removed with a scalpel. The surgeon then seats the implant to determine if any conical extensions must be trimmed to establish the proper height. The edges of the implant 28 must align and make a smooth transition with the outer surface of the cranium 30.

As shown in FIG. 6, a number of conical extensions have been trimmed to varying degrees at areas A, B and C and the implant substantially fills the defect. The planar section of the implant is in contact with the lateral walls 30 of the cranium and the conical extensions contact the bottom of the graft bed 32. After a fit is established with good edge to edge contact, screws can be obliquely set through the implant to firmly secure the device in place. For additional support, the surgeon can first create a seat for the implant on the outer table with a low speed bur. As an alternative to screws, the implant can be held in place by pressure fitting within the edges of the cranial opening or with wire sutures until ossification permanently stabilizes the implant.

Although the elasticity of the implant will depend on the actual material from which the implant is constructed, "MEDPOR" is somewhat elastic and after flexation tends to return to its original shape. Because of its elasticity, it is recommended to retained the device in place with wire sutures or surgical screws in order to keep the device in a fixed position until it is stabilized by tissue ingrowth. An implant made of MEDPOR™ can be heated in a solution of physiologic saline to allow for easier bending and, upon cooling, the implant will retain is new shape. The device can also be forced fit within the radial sidewalls of the defect which will retain the implant in position until the surrounding tissue grows into the pores. Once new bone and soft tissue grows into the porous structure, the implant is adequately stabilized.

When the implant is placed in edge to edge engagement with the outer table of the cranium, rapid bone growth into the implant occurs which can reach up to several millimeters. The ingrowth of this bone tissue forms a strong and stable connection between the cranium and the implant. In the treatment of calvarial graft donor sites, the surgeon can take advantage of a bed graph site which can initiate ingrowth of new bone material from both the lateral walls 30 and bottom of the bed site 32. Tissue from the scalp or periosteum can penetrate the top surface 16 of the implant to provide additional stability to the implant.

The shape of the implant allows limited flexibility while retaining thickness. In instances where the void communicates with the dura, the dura tissue can grows upward into the substrate and the voids 34 located between the conical extensions. The outer table of the cranium grows into the porous substrate from the lateral sidewalls of the defect and can become ossified. Tissue ingrowth from each of the contiguous surfaces Permanently stabilizes the implant in the defect.

Having thus described the present invention and its preferred embodiment in detail, it will be readily apparent to those skilled in the art that further modifications to the invention may be made without departing from the spirit and scope of the invention as presently claimed.

We claim:

1. A bone implant comprising a substrate with a flat smooth continuous planar upper surface, and a lower surface having a plurality of projections extending transversely to the plane of said upper surface evenly and uniformly distributed over the entire said lower surface, said projections being porous and having pores capable of supporting tissue ingrowth and being spaced from each other in two dimensions over said lower surface, the spacing between the projections permitting said implant to be flexed about an axis extending in any direction parallel with said upper surface with the flexing occurring in said substrate between said projections.

2. The implant disclosed in claim 1, wherein said projections are conical.

3. The implant as disclosed in claim 1, wherein said porous substrate comprises high density polyethylene.

4. The implant according to claim 1, wherein said implant can be cut with a pair of surgical scissors or bone cutters.

5. The bone implant disclosed in claim 1, wherein said projections have a circular cross section.

6. The implant as disclosed in claim 1, wherein said projections have axial dimensions and wherein said flat upper surface defines the upper surface of a planar region having a thickness less than the axial dimension of the majority of said projections.

7. A bone implant as recited in claim 1, wherein said projections have bases at which said projections are joined to said lower surface, said bases being spaced from one another so that portions of said lower surface substantially parallel to said upper surface extend between said bases.

8. A bone implant as recited in claim 7, wherein said projections are conical.

9. The implant as recited in claim 1 wherein said both the upper and lower surface have pores sized to allow for tissue ingrowth.

10. The implant as recited in claim 1 wherein said implant is homogenous.

11. The implant as recited in claim 1 wherein a base area of each said projections tapers to a terminal end and an axial section through said projection at said base area has a larger area than an axial section through said projection at said terminal end.

12. A tissue implant comprising a porous polyethylene homogenous substrate having pores capable of supporting tissue ingrowth with a flat upper surface, and a lower surface having a plurality of porous projections evenly and uniformly distributed over a major portion of said lower surface.

13. A bone implant comprising a substrate with a flat smooth continuous planar upper surface, and a lower planar surface having a plurality of projections extending transversely to said lower planar surface evenly and uniformly distributed over the entire said lower surface, said projections being porous and having pores capable of supporting tissue ingrowth and spaced from one another so that the implant may be flexed about an axis extending in any direction parallel with said upper surface.

14. A flexible bone implant comprised of porous plastic capable of supporting tissue ingrowth having an upper flat, smooth, continuous, planar surface and a lower planar surface having a plurality of conical projections extending therefrom, said projections being porous and arranged in at least one row, said lower planar surface further having interstitial planar regions between neighboring projections, said interstitial planar regions further defined by being parallel with said upper flat, smooth, continuous, planar surface, and said implant being flexible about an axis extending in any direction parallel with said upper surface.

15. A flexible bone implant comprised of porous plastic capable of supporting tissued ingrowth having an upper flat, smooth, continuous, planar surface and a lower planar surface having a plurality of porous projections extending therefrom transversely from said lower planar surface, interstitial regions of said lower surface being between neighboring projections, each said interstitial region being parallel with said upper planar surface, and said implant being flexible about an axis extending in any direction parallel with said upper surface.

16. A flexible bone implant as recited in claim 15, wherein said projections are frustroconical.

\* \* \* \* \*